United States Patent [19]

Gross

[11] 4,017,653

[45] Apr. 12, 1977

[54] ABSORBENT ARTICLES AND METHODS FOR THEIR PREPARATION

[75] Inventor: James R. Gross, Lake Jackson, Tex.

[73] Assignee: The Dow Chemical Company, Midland, Mich.

[22] Filed: May 1, 1975

[21] Appl. No.: 573,661

Related U.S. Application Data

[60] Division of Ser. No. 468,794, May 9, 1974, Pat. No. 3,980,663, which is a continuation-in-part of Ser. No. 371,909, June 20, 1973, abandoned.

[52] U.S. Cl. .................. 427/385 A; 128/156; 128/270; 128/285; 264/129; 264/331; 427/385 B; 427/386; 427/388 A
[51] Int. Cl.² .................. B05D 3/02; C08L 31/02; C08L 33/02
[58] Field of Search .................. 128/156, 270, 285; 156/247; 260/2.1 R, 2.1 E, 2.1 M; 264/212, 216, 331, 129; 427/385 A, 385 B, 386, 401, 388 A

[56] References Cited

UNITED STATES PATENTS

| | | | |
|---|---|---|---|
| 3,245,933 | 4/1966 | Muskat | 260/29.6 |
| 3,467,604 | 9/1969 | Michaels | 260/2.5 |

Primary Examiner—Michael R. Lusignan
Attorney, Agent, or Firm—Benjamin G. Colley

[57] ABSTRACT

Water swellable absorbent articles, made from carboxylic polyelectrolytes, together with methods for their preparation, and a composition useful to make said articles are disclosed. The articles are crosslinked by heating and/or removing substantially all of the water from the precursor composition.

The absorbent articles are useful as surgical sponges, diapers, tampons, meat trays, bath mats, and the like.

15 Claims, No Drawings

ABSORBENT ARTICLES AND METHODS FOR THEIR PREPARATION

CROSS REFERENCE TO RELATED APPLICATIONS

This application is a divisional application of Ser. No. 468,794 filed May 9, 1974 now U.S. Pat No. 3,980,663, patented Sept. 14, 1976, which is a continuation-in-part of Ser. No. 371,909, filed June 20, 1973 which is now abandoned.

BACKGROUND OF THE INVENTION

This invention relates to water swellable absorbent articles made from crosslinked polyelectrolytes, methods for their preparation, and to a composition consisting of polyelectrolytes which is useful to make absorbent articles.

It is known from U.S. Pat. Nos. 3,669,103 and 3,670,731 that cross-linked polymeric sorbents can be sandwiched between flexible supports to achieve disposable diapers or dressings.

It is further known from U.S. Pat. Nos. 2,988,539; 3,393,168; 3,514,419 and 3,357,067 that water swellable cross-linked carboxylic copolymers can be prepared. However, these prior art copolymers are all crosslinked during copolymerization or crosslinked after polymerization with subsequent neutralization of the carboxylic acid groups to form water swellable polyelectrolytes and hence these prior art polyelectrolytes cannot be crosslinked in situ as a coating on a substrate or as a flexible film thereof.

SUMMARY OF THE INVENTION

The present invention comprises a composition which is useful to form water swellable articles of a carboxylic type synthetic polyelectrolyte which consists of lower alcohols, water, or mixtures thereof, about 5 to about 60 percent, preferably about 15 to about 40 percent by weight based on the solvent of a carboxylic polyelectrolyte, and at least about 0.1 percent, and preferably not more than about 10 percent by weight based on the polyelectrolyte of a crosslinking agent reactive with carboxylate groups. The crosslinking agent can be selected from classes such as polyhaloalkanols, sulfonium zwitterions, haloepoxy alkanes, polyglycidyl ethers, and mixtures thereof.

The invention further comprises methods of making discrete films, absorbent articles, particulates, fibers, and the products of these processes wherein the above composition on various substrates, is heated to a temperature greater than about 30° C. and preferably from about 90° to about 150° C. The use of these elevated temperatures is advantageous to accelerate the crosslinking and drying of the polyelectrolyte. However, if desired, the use of heat can be eliminated.

In order to obtain very high production rates of absorbent articles, it may be desirable to replace part or nearly all of the water in the polyelectrolyte solution with a lower alcohol such as methanol or ethanol. This substitution results in lower solution viscosities at a given percent solids and promotes rapid drying.

The final products of the present invention are thus water swellable and are useful where ever aqueous solutions need to be absorbed. Examples of the diverse utilities are surgical sponges, catamenial tampons, diapers, meat trays, paper towels, disposable door mats, disposable bath mats and disposable litter mats for household pets.

DETAILED DESCRIPTION

Examples of carboxylic synthetic polyelectrolytes useful in this invention are the ammonium or alkali metal salts of homopolymers of acrylic or methacrylic acid and copolymers with one or more ethylenically unsaturated comonomers. The only limitation being that any copolymer, to be useful in preparing highly absorbent polymers according to this invention, must be essentially water soluble in the salt form. The alternating copolymers of maleic anhydride and the maleic and fumaric acids and esters are useful when rendered water soluble by an appropriate base. One skilled in the art of radical addition copolymerization could prepare any number of suitable heteropolymers containing sufficient carboxylate functionality to render them water soluble and thus be useful in this invention.

A list of applicable carboxylic polymers which could be prepared from readily available monomers and converted into their salt form is as follows:

acrylic acid — acrylate copolymers
acrylic acid — acrylamide copolymers
acrylic acid — olefin copolymers
polyacrylic acid
acrylic acid — vinyl aromatic copolymers
acrylic acid — styrene sulfonic acid copolymers
acrylic acid — vinyl ether copolymers
acrylic acid — vinyl acetate copolymers
acrylic acid — vinyl alcohol copolymers
copolymers of methacrylic acid with all the above comonomers
copolymers of maleic acid, fumaric acid and their esters with all the above comonomers
copolymers of maleic anhydride with all the above comonomers.

If desired, the foregoing polyelectrolytes can also be sulfonated by treatment with $SO_3$, chlorosulfonic acid or fuming sulfuric acid in an inert organic solvent.

Illustrative examples of the crosslinking agents useful in this invention are polyhaloalkanols such as 1,3-dichloroisopropanol; 1,3-dibromoisopropanol; sulfonium zwitterions such as the tetrahydrothiophene adduct of novolac resins; haloepoxyalkanes such as epichlorohydrin, epibromohydrin, 2-methyl epichlorohydrin, and epiiodohydrin; polyglycidyl ethers such as 1,4-butanediol diglycidyl ether, glycerine-1,3-diglycidyl ether, ethylene glycol diglycidyl ether, propylene glycol diglycidyl ether, diethylene glycol diglycidyl ether, neopentyl glycol diglycidyl ether, polypropylene glycol diglycidyl ethers having an epoxy equivalent weight range from about 175 to about 380, bisphenol A-epichlorohydrin epoxy resins having an epoxy equivalent weight range from about 182 to about 975 and mixtures of the foregoing.

Compounds containing two or more of the functional groups of the foregoing crosslinking agents would be expected to be likewise useful, as well as precursors which would form these functional groups under the conditions encountered in heating or drying the polyelectrolyte solutions.

Sulfonium zwitterions are known from U.S. Pat. No. 3,660,431 dated May 2, 1972; Ser. No. 205,754 and Ser. No. 205,755 both filed on Dec. 7, 1971. The disclosures of this patent and patent applications are incorporated herein by reference.

The crosslinking technique used in this invention to transform soluble polyelectrolytes into insoluble but water swellable polymers is known as nucleophilic displacement on saturated carbon.

The carboxylate ion on the polyelectrolyte acts as the nucleophile while the cross-linking agent is the substrate for the nucleophilic attach. Typical leaving groups and their corresponding substrates are listed in the following table. Any combination of two or more of these leaving groups on the same substrate could act as a cross-linking agent for polycarboxylates.

Table I

| Leaving Groups in Nucleophilic Displacement ($R'$ = alkyl or aryl) | |
|---|---|
| Leaving Group | Substrate |
| $Cl^-$ | Alkyl chloride R-Cl |
| $Br^-$ | Alkyl bromide R-Br |
| $I^-$ | Alkyl iodide R-I |
| $HO^-$ | Alcohol R-OH |
| $RO^-$ | Ether ROR, $R\overset{O}{\diagup\diagdown}R$ |
| $R'C\overset{O}{\underset{\parallel}{-}}O^-$ | Ester $R-O\overset{O}{\underset{\parallel}{C}}-R'$ |
| $^-OSO_2R'$ | Alkyl sulfonate $R-OSO_2R'$ |
| $^-OSOCl$ | Alkyl chlorosulfite ROSOCl |
| $^-OPCl_2$ | Alkyl chlorophosphite $R-OPCl_2$ |
| $^-OPBr_2$ | Alkyl bromophosphite $R-OPBr_2$ |
| $^-OSOR'$ | Alkyl sulfinite ROSOR' |
| $NR_3$ | Tetraalkyl ammonium ion $R-N^+R_3$ |
| $N_2$ | Alkyl diazonium ion $R-N^+\equiv N$ |
| $SR'_2$ | Trialkyl sulfonium ion $R-S^+R'_2$ |

Table II. lists several illustrative compounds used as cross-linking agents in this invention and the operable limits to obtain insoluble but highly swellable polyelectrolytes according to this invention. Once insolubility is reached, higher levels of cross-linker give polymer which swells in aqueous media to produce firmer, less slippery gels but of lower actual absorbency.

Table II

| Cross-linking Agents for Polycarboxylates | |
|---|---|
| Cross-linker | (Wt.% of polyelectrolyte) Level of Incorporation |
| 1,3-dichloroisopropanol | 1 – 10% |
| epibromohydrin | 0.5 – 10% |
| epichlorohydrin | 1 – 10% |
| glycerine diglycidyl ether | 0.10 – 45% |
| novolac sulfonium ion | 1 – 10% |

The rate of nucleophilic displacement is concentration dependent and is a factor in this invention. In a composition, when the concentration of the cross-linker is very low, the rate of reaction is quite slow (pot life 10–48 hours before gelation). Once the composition is applied to a substrate surface and evaporation of solvent begins, the rate of cross-linking accelerates. Applying heat at this time increases the reaction rate even more.

If the cross-linking reaction is allowed to proceed in the original composition as by heating, aging, or excessive amounts of cross-linker, the absorbent articles of this invention cannot be fabricated. The composition will become progressively more viscous and stringy until it forms a continuous gel which could not be spread, sprayed or spun.

In the preferred method of making water swellable films by the present invention, the above composition of the polyelectrolytes is spread on a flat plate or roller of metal, plastic, or other impervious substrate and heated to a temperature greater than 30° C. to crosslinke the polyelectrolyte and drive off the excess water and/or alcohol. The film is then peeled off the plate or roller by a scraper to recover the intact film for subsequent storage or use.

It is sometimes desirable to add a small amount of a surfactant to the polyelectrolyte composition to aid in flowing on and removing the continuous film from the water impervious substrate. A secondary benefit of using a surfactant is to increase the wettability of the final dry absorbent film. Either anionic or nonionic surfactants may be used. Examples of the useful surfactants are the sodium alkyl sulfonates and ethylene oxide derivatives of alkylated phenols and the like.

Similarly, when an absorbent article is prepared, the article which is to be the substrate is coated with the composition of the polyelectrolyte and then the coating is crosslinked. It is to be understood that for the purposes of this invention the coating step implies a complete coating or a discontinuous coating, thus when a fiberous substrate such as cellulose batting, paper, woven or non-woven cloth, and the like are used as the substrate, the composition can be applied in a discontinuous manner, i.e., in a pattern of large dots, squares, or grid lines to retain the inherent flexibility of the fiberous substrate and at the same time vastly improve its water absorbency. In this instance plasticizers are not needed. Wood pulp can be coated by slurrying it in the polyelectrolyte composition followed by a fluffing operation.

If desired, the water swellable film prepared as above can be used per se as the inner absorbent layer in baby diapers. It is sometimes advantageous that the film be disintegrated into flakes, strips or powders. This is accomplished by crushing or comminuting the film in a hammer mill, blenders, or the like. If long flat strips are desired, the film can be sliced widthwise with appropriate slicers.

In some instances, water swellable fibers are desired. These can be prepared by extruding the above composition of the polyelectrolytes into a bath comprising lower alkyl ketones such as acetone, methyl ethyl ketone, diethyl ketone and the like. Alcoholic compositions may be extruded into a non-aqueous coagulant such as chlorinated hydrocarbons, i.e., methylene chloride, perchloroethylene and the like. The soft extruded fibers are then removed from the bath by any convenient means such as a three or five roll cluster and carried through a heated chamber at a temperature greater than about 30° C and preferably in the range from about 70° to about 150° C. to dry and to crosslink the polyelectrolyte fibers.

The absorbency of the crosslinked polyelectrolytes (grams solution gelled per gram of polyelectrolyte) is determined in the following manner using snythetic urine (0.27 N sodium chloride solution).

A 0.5 gram sample of a crosslinked polyelectrolyte is weighed into a 250 ml. beaker, a 0.27 N sodium chloride solution (150 ml.) is poured into the beaker and allowed to soak for 2 hours at room temperature, with occasional stirring. The swelled polyelectrolyte is then collected by filtration and the gel capacity is reported as grams of solution gelled per gram of polymer salt.

The following examples are presented solely to illustrate but not limit the invention.

EXAMPLE 1

A solution (22% solids) of the disodium salt of poly(isobutylene-co-maleic anhydride) was prepared in deionized water. To 14.7 g. of this solution was added 0.28 g. (8.7% by weight solids) of 1,3-dichloroisopropanol. Ten drops of a 2% solution of sodium lauryl sulfonate were also mixed in. After standing for 40 minutes to become bubble-free, the solution was spread on clean polyethylene sheeting with a 25 mil draw bar. The film separates from the polyethylene upon drying. After drying overnight, the film is still water soluble. After 30 minutes at 60° C. the film absorbs 64 times its own weight of 0.27 N NaCl without dissolving. After 1 hour at 100° C. the absorbency (gel capacity) is 25 g. of 0.27 N NaCl per gram of film indicating the crosslinking reaction is essentially complete.

EXAMPLE 2

A 25% aqueous solution of poly(isobutylene-co-disodium maleate) was prepared and 10 g. of this solution mixed with 0.2 g. (8%) epibromohydrin, one ml. water, and 4 drops of 2% sodium lauryl sulfonate. A film was drawn on Mylar, lifted from the Mylar sheet and cured at 100° C. for 2 hours. The film gave an absorbency of 56 g/g in 0.27 N NaCl solution.

EXAMPLE 3

Example 2 was repeated using only 0.05 g. (2%) of epibromohydrin. This film absorbs 76 times its own weight of 0.27 N NaCl without dissolving.

EXAMPLE 4

Rohm and Haas Acrysol A-5 (polyacrylic acid, 25% solids in water) was neutralized with a stoichiometric amount of NaOH and treated with 10% by weight epibromohydrin and a film drawn on Mylar. After drying overnight at 85° C. this film gave an absorbency of 54 g/g in 0.27 N NaCl.

EXAMPLE 5

Example 2 was repeated using 0.25 g. (10% by weight solids) epichlorohydrin as the crosslinking agent. After drying at 70° C. overnight a film gave an absorbency of 92 g/g in 0.27 N NaCl.

EXAMPLE 6

Example 4 was repeated using 1.0% by weight glycerine diglycidyl ether and 20% by weight Methocel MC 25 (a methyl cellulose having a viscosity of 25 cps for a 2% aqueous solution) as a plasticizer. After drying overnight at room temperature the film was grainy but flexible. After curing for 2 hours at 70° C. the film absorbed 33.6 g/g of 0.27 N NaCl and 226 g/g of deionized water.

EXAMPLE 7

A 25% solution in water of poly(isobutylene-co-ammonium-half amide maleate) was treated with glycerine diglycidyl ether (10% by weight based on the polymer), glycerine (30% by weight polymer), and 10 drops of 2% sodium lauryl sulfonate. A film was drawn on a sheet of Mylar and allowed to stand at room temperature overnight. The absorbency in 0.27 N NaCl of this film was 10.2 g. solution/gram polymer.

EXAMPLES 8–14

Example 2 was repeated using various amounts of glycerine diglycidyl ether for the crosslinker in place of epibromohydrin and 30% by weight based on the polymer of glycerine as a plasticizer. Films were drawn on a sheet of Mylar and allowed to cure overnight at room temperature. The results are set forth in Table III.

Table III

| Example | Glycerine Diglycidyl Ether Weight Percent Polymer | Gel Capacity in 0.27 N NaCl, g/g |
|---|---|---|
| 8 | 1 | 52 |
| 9 | 2 | 35 |
| 10 | 3 | 36 |
| 11 | 4 | 26 |
| 12 | 5 | 28 |
| 13 | 6 | 26 |
| 14 | 30 | 14 |

Table III illustrates the greater reactivity (efficiency) of glycerine diglycidyl ether compared to the haloalkanols and haloepoxides. Not only is much less required to effectively cure the polyelectrolyte but the curing takes place at room temperature.

EXAMPLE 15

An 8% aqueous solution of Purifloc N-17 acrylamide-sodium acrylate copolymer was treated with 10% by weight (of the polymer) glycerine diglycidyl ether, 25% by weight glycerine, 15 drops of 2% sodium lauryl sulfonate and formed into a film. After drying overnight at room temperature and curing for 30 minutes in an 80° C. oven, the film gave a gel capacity in 0.27 N NaCl of 15 g/g.

EXAMPLE 16

A laboratory paper towel was coated from an aqueous solution consisting of 10 g. of 25% solids poly(isobutylene-co-disodium maleate), 10 drops of 2% sodium lauryl sulfonate, and 0.05 g. (2.0%) of epibromohydrin. When dry the coating amounted to 36% of the total weight of the coated towel. This coated paper had an absorbency in deionized water of 14.3 g/g towel compared to 2.54 g/g for untreated toweling.

EXAMPLE 17

A foamed polystyrene meat tray was coated with an aqueous solution consisting of 20 g. of 22% solids poly(isobutylene-disodium maleate) and 0.17 g. (4%) dichloroisopropanol. After drying overnight the weight of the coating was 0.7 g. The coated tray absorbed 13.5 g. of 0.27 N NaCl solution for a capacity of 19 g. solution/g coating.

EXAMPLE 18

The ammonium-halfamide salt of an ethylene-maleic anhydride copolymer (82 cps viscosity for 5% solution in water) was made up as a 25% solution in water. 8.0 g. of this solution was blended with 0.7 g. glycerine, 0.05 g. (2.5% by weight solids) glycerine diglycidyl ether, and 10 drops of 2% sodium lauryl sulfonate. The solution was drawn on a Mylar sheet using a 15 mil bar and allowed to cure at room temperature for 2 days. This film gave an absorbency of 16 g. of 0.27 N NaCl per gram of film.

EXAMPLE 19

The ammonium-halfamide salt of a styrene-maleic-anhydride copolymer (173 cps. for 5% solution in water) was treated as in Example 18 above. This film gave an absorbency of 5.4 g/g film in 0.27 N NaCl.

EXAMPLE 20

Example 19 was repeated using only 1% by weight polymer of glycerine diglycidyl ether. This film absorbed 13.2 g/g 0.27 N NaCl after curing overnight at room temperature.

EXAMPLE 21

The disodium salt of a methyl vinyl ether maleic anhydride copolymer (GAF Gantrez AN 169) was prepared in water at 15% solids and a film was formed as in Example 18 using 3.3% glycerine diglycidyl ether as a cross-linker. After curing overnight at room temperature the film absorbed 15.4 times its own weight of 0.27 N NaCl.

EXAMPLE 22

Isobutylene maleic anhydride copolymer (15.4 g., 0.1 mole) was slurried in 200 ml. methyl alcohol and 1 ml. pyridine was added. The mixture was stirred at 50° C. for 24 hours to yield a clear solution. The polymer was precipitated in water, dried in a vacuum oven and dissolved in dilute aqueous caustic to yield a 25% solution of the sodium salt of the methyl half ester of the copolymer.

A film was formed by treating 10 g. of this solution with 29 mg. (1.16 wt.%) glycerine diglycidyl ether and 10 drops of 2% sodium lauryl sulfonate and spreading the solution on a sheet of Mylar with a 25 mil drawbar. After curing overnight at room temperature, the polymer was insoluble and absorbed 352 g/g of deionized water and 39 g/g of 0.27 N NaCl.

When the cross-linker level was lowered to 17 mg. (0.68 wt.%) the resulting film absorbed 55.6 g/g dilute salt solution and 720 g/g deionized water. The cross-linking reaction was not complete as this same film absorbed 27 g/g salt solution after being placed in 90° C. oven for 30 minutes.

EXAMPLE 23

A 40% solids aqueous solution of poly(isobutylene-co-disodium maleate) was prepared by dissolving the anhydride form of the copolymer in the calculated amount of sodium hydroxide and water. 20 g. of this solution was blended with 0.4 g. (5% by weight polymer) glycerine diglycidyl ether. An extrusion chamber (¾ inch by 2 inches pipe with bottom ball valve and 1/16 inch tubing outlet as an extruder tip) was filled and the dope extruded vertically into a 12 inches deep coagulation bath of acetone. The single filament was allowed to pile up on the bottom of the bath and was pulled out at the end of the run. Nitrogen, under a pressure of 25 psig, was used to pressure the spinning dope through the extruder tip.

After drying for 2 hours at 100° C., the fiber was checked for absorbency. It absorbed 28 g/g of synthetic urine (0.27 N NaCl) and 138 g/g of deionized water.

EXAMPLE 24

A film was cast on Mylar sheeting from a 25% aqueous solution of poly(isobutylene-co-disodium maleate) blended with 25% glycerine by weight polymer and 2.5% glycerine diglycidyl ether. The film was cured at 80° C. for 1 hour and then allowed to equilibrate with the 50% relative humidity in the room. The film was slit into ¾ inch strips which were then chopped into a flat staple of approximately 2 mm width. The staple rapidly absorbed 14 times its own weight of synthetic urine and 55 times its own weight of deionized water.

EXAMPLE 25

A 25% solids aqueous solution of the disodium salt of isobutylene maleic anhydride copolymer was blended with a few drops of 2% sodium lauryl sulfonate and 5% by weight of the copolymer of the aryl sulfonium zwitterion as set forth in Example 3B of U.S. Pat. No. 3,660,431.

A film was formed and dried at 100° C. for 13 hours. The cloudy film absorbed 58 times its own weight of synthetic urine and 300 times its weight of deionized water.

EXAMPLE 26

A film was prepared from a 25% aqueous solution of disodium isobutylene/maleic anhydride copolymer with 0.75% by weight glycerine diglycidyl ether. After curing at 100° C. for 3 hours the film absorbed 72 g/g of synthetic urine. The dry film was crushed into small flakes exhibiting the same absorbency and ground in a mortar to a fine powder which quickly absorbed synthetic urine to the degree of 74 g/g powder.

EXAMPLES 27 – 32

A 7.5% aqueous solution of poly(sodium acrylate-co-methylacrylate), 80% sodium acrylate, was prepared from a latex of poly(methylacrylate) by adding sodium hydroxide and diluting with water. Using various amounts of glycerine diglycidyl ether as a cross-linker, films were drawn on glass plates and cured in an oven at 125° C. for 1 hour. The results are set forth in Table IV.

Table IV

| Example | Glycerine Diglycidyl Ether Weight Percent Polymer | Gel Capacity in 0.27 N NaCl, g/g |
| --- | --- | --- |
| 27 | 2.5 | 17 |
| 28 | 1.0 | 19 |
| 29 | 0.5 | 25 |
| 30 | 0.25 | 41 |
| 31 | 0.10 | 98 |
| 32 | 0.00 | 0, Soluble |

Table IV shows that, while very little curing agent is needed, without any the polyelectrolyte is not water swellable even after the film is dried and heated. For good firm aqueous gels, at least 0.1% by weight is needed, the exact amount depending on the polymer, curing, and end-use application.

EXAMPLE 33

A 25% aqueous solution of a 90/10 copolymer of sodium styrene sulfonate and sodium acrylate was prepared by heating the monomer solution overnight at 50° C. in the presence of 0.04% by weight $K_2S_2O_8$ (Potassium persulfate). 8 g. of this solution mixed with 75 mg. (3%) of glycerine diglycidyl ether and a film was cast on Mylar. After air drying for 2 hours, the film was lifted and placed in a 90° oven for 1 hour. The gel capacity was 45 g/g of 0.27 N NaCl.

EXAMPLE 34

A 25% solution of polyacrylic acid (Rohm and Haas Acrysol A-5) was treated with one equivalent of sodium hydroxide and diluted to 20% solids. Ten grams of this solution was then blended with 800 mg. of a 5% solution of D.E.R. 736 in n-butanol for 2% D.E.R. 736 by weight polymer. D.E.R. 736 is the diglycidyl ether of 250 mol. wt. polypropylene glycol having an E.E.W. of 175-205. A film was cast on a chrome plate, air dried for 3 days then cured in an oven at 150° C. for 2 hours.

The dried and cured film (0.5 g.) was dispersed in 150 ml. of 0.27 N NaCl solution and allowed to soak for 1 hour after which the swollen polymer was recovered on a 150 mesh screen and weighed. The gel weighed 41 grams for an absorbency of 82 g. per gram polymer.

EXAMPLE 35

A 50% aqueous solution of poly(ethylene-co-monobutyl maleate) Monsanto EMA 3122 was treated with one equivalent of sodium hydroxide and diluted to 25% solids.

This solution was blended with 1.5% D.E.R. 736 as in Example 33 and the film was prepared and tested. The absorbency was 39 grams per gram of polymer.

EXAMPLES 36-44

Three mixtures were made up having the following compositions.

| Part A | Part B | Part C |
|---|---|---|
| 600 g. deionized water | 437.5g. ethyl acrylate | 175g. deionized water |
| 0.75g. Triton GR-5* | 77.2g. methacrylic acid | 2.0g. sodium bisulfite |
| 1.75g. sodium persulfate | | |

*dioxtylsodium sulfosuccinate.

Part A was charged to a 2 liter reactor and brought to 40° C. while under vigorous nitrogen purge. 18 milliliters of Part B was added to the reactor followed by all of Part C. The remainder of Part B was added over the next 2.5 hours while the temperature was held at 39°-41° C. The latex was then digested at 60° C. for 1.5 hours, cooled to 30° and bottled. The latex contained 40.6 percent by weight non-volatiles.

1125 g. of the above latex was added in a small stream over a period of 25 minutes to a slowly stirred solution of 187.16 g. 50% NaOH in 547.9 g. deionized water. After the polymer had all dissolved, the viscous solution was heated at 50° C. for 22 hours to complete the saponification. The resulting solution (25.4% solids) had a Brookfield viscosity of 16,200 cps. at 25° C. (No. 5 spindle, 10 rpm). The polymer is 50% ethylacrylate by moles with the remainder being sodium acrylate and methacrylate.

Samples of the above solution were blended with D.E.R. 736 epoxy resin and cast on polished chromium plate with a 25 mil draw bar. After air drying, the films were lifted from the plate and placed in a 150° oven for 2 hours. The absorbency (gel capacity) of the various films in 0.27 N. NaCl is set forth in Table V.

Table V

| Example | Weight % D.E.R. 736 | Weight %* Acetone | Absorbency |
|---|---|---|---|
| 36 | 0.15 | 0 | 57.4 |
| 37 | 0.2 | 0 | 36.2 |
| 38 | 0.25 | 0 | 34 |
| 39 | 0.25 | 20 | 37.4 |
| 40 | 0.5 | 20 | 28.2 |
| 41 | 1.0 | 20 | 19.5 |
| 42 | 5.0 | 20 | 6.4 |
| 43 | 5.0 | 0 | 10.4 |
| 44 | 10.0 | 0 | 7.2 |

*D.E.R. 736 first dissolved in 2 g. acetone then dispersed in 8 g. of 25% polymer solution.

Table V illustrates that with essentially water insoluble epoxy resins, a co-solvent or carrier such as acetone is needed to obtain efficient cross-linking at higher levels of curing agent. At very low levels, the epoxy resin alone is dispersed well enough to react efficiently.

EXAMPLES 45-52

The procedure of Examples 36-44 was repeated using a 20% aqueous dispersion of D.E.R. 661 (a bisphenol A-epichlorohydrin epoxy resin having an epoxy equivalent weight range of 475-575). The films thus prepared were tested in the same manner. The results are set forth in Table VI.

Table VI

| Example | Weight % D.E.R. 661 | Weight % Acetone | Absorbency |
|---|---|---|---|
| 45 | 2.0 | 20 | 78 |
| 46 | 2.5 | 20 | 40.6 |
| 47 | 3.0 | 20 | 46.6 |
| 48 | 3.0 | 0 | 3.6 |
| 49 | 4.0 | 20 | 38.4 |
| 50 | 5.0 | 20 | 32.4 |
| 51 | 5.0 | 0 | 28.8 |
| 52 | 10.0 | 0 | 19.4 |

Table VI shows the behavior of a solid, water insoluble epoxy resin. Without a co-solvent, the resin reacts with the polyelectrolyte only on the surfaces of the resin particles and is very inefficient. After swelling in the co-solvent, the cross-linking efficiency is significantly improved.

EXAMPLES 53-61

The procedure of Examples 36-44 was again repeated using the diglycidyl ether of neopentyl glycol as the curing agent. The results are set forth in Table VII.

Table VII

| Example | Weight % DGENG* | Weight % Acetone | Absorbency |
|---|---|---|---|
| 53 | 0.15 | 0 | 80 |
| 54 | 0.20 | 0 | 40.6 |
| 55 | 0.25 | 0 | 47.6 |
| 56 | 0.5 | 20 | 31.4 |
| 57 | 1.0 | 20 | 21.6 |
| 58 | 2.5 | 20 | 11.8 |
| 59 | 5.0 | 20 | 9.2 |
| 60 | 5.0 | 0 | 12 |
| 61 | 10.0 | 0 | 5.8 |

*DGENG is the diglycidyl ether of neopentyl glycol.

EXAMPLES 62-68

The procedure of Examples 36-44 was repeated using the diglycidyl ether of 1,4-butanediol (DGEBD)

as the curing agent. The results are set forth in Table VIII.

Table VIII

| Example | Weight % DGEBD | Weight % Acetone | Absorbency |
|---|---|---|---|
| 62 | 0.15 | 0 | 59.8 |
| 63 | 0.20 | 0 | 44.6 |
| 64 | 0.5 | 20 | 21.8 |
| 65 | 1.0 | 20 | 20.2 |
| 66 | 5.0 | 20 | 7.6 |
| 67 | 5.0 | 0 | 9.2 |
| 68 | 10.0 | 0 | 6.4 |

I claim:

1. A method of preparing an absorbent article coated with a substantially dry water swellable polyelectrolyte which comprises
    a. applying a coating on a relatively thin article wherein the coating comprises
        1. a solution of a carboxylic synthetic polyelectrolyte wherein the solution consists of water, lower alcohols, or mixtures thereof and about 5 to about 60% by weight of a carboxylic polyelectrolyte, and
        2. at least about 0.1% by weight based on the polyelectrolyte of a crosslinking agent reactive with carboxylate groups,
    B. heating said coated article to a temperature greater than about 30° C. to crosslink said polyelectrolyte.

2. The method of claim 1 wherein the article is a natural or a synthetic fibrous substrate.

3. The method of claim 1 wherein the article is a synthetic film.

4. The method of claim 1 wherein the article is a foamed polymer.

5. The coated article produced by the method of claim 1.

6. The coated article produced by the method of claim 2.

7. The coated article produced by the method of claim 3.

8. The Coated article produced by the method of claim 4.

9. A method as set forth in claim 1 wherein the crosslinking agent is present in the range from 0.1 - 10% by weight.

10. A method as set forth in claim 1 wherein the carboxylic polyelectrolyte consists of a terpolymer of ethyl acrylate, sodium acrylate, and sodium methacrylate with 50 mole percent being ethyl acrylate.

11. A method as set forth in claim 1 wherein the carboxylic polyelectrolyte consists of polysodium acrylate.

12. A method as set forth in claim 1 wherein the carboxylic polyelectrolyte consists of poly(isobutylenecodisodium maleate).

13. A method as set forth in claim 1 wherein the crosslinking agent is the diglycidyl ether of polypropylene glycol.

14. The method as set forth in claim 1 wherein said crosslinking agent is selected from polyhaloalkanols, sulfonium zwitterions, haloepoxyalkanes, polyglycidyl ethers, and mixtures thereof.

15. The method as set forth in claim 1 wherein the crosslinking agent is a polyglycidyl ether.

* * * * *